United States Patent [19]

Theriot et al.

[11] Patent Number: 5,744,676
[45] Date of Patent: Apr. 28, 1998

[54] OLEFIN OLIGOMERIZATION PROCESS

[76] Inventors: Kevin J. Theriot, 7565 Sheringham Ave., Baton Rouge, La. 70808; Robert G. Irwin, 15010 Ridgewood Ave., Prairieville, La. 70869

[21] Appl. No.: 606,669

[22] Filed: Feb. 26, 1996

[51] Int. Cl.[6] .................................. C07C 2/08
[52] U.S. Cl. .................. 585/510; 585/511; 585/525
[58] Field of Search ................... 585/510, 511, 585/525

[56] References Cited

U.S. PATENT DOCUMENTS

| | | | |
|---|---|---|---|
| 2,500,161 | 3/1950 | Seger et al. | 260/683.15 |
| 2,500,163 | 3/1950 | Garwood | 260/683.15 |
| 2,766,312 | 10/1956 | Serniuk | 260/683.15 |
| 2,806,072 | 9/1957 | Cohen et al. | 260/683.15 |
| 3,382,291 | 5/1968 | Brennan | 260/683.15 |
| 3,686,351 | 8/1972 | Mason | 585/525 |
| 3,769,363 | 10/1973 | Brennan | 260/683.15 B |
| 3,997,621 | 12/1976 | Brennan | 260/683.15 B |
| 4,172,855 | 10/1979 | Shubkin et al. | 585/16 |
| 4,218,330 | 8/1980 | Shubkin | 252/46.6 |
| 4,409,415 | 10/1983 | Morganson et al. | 585/525 |
| 4,436,947 | 3/1984 | Morganson et al. | 585/525 |
| 4,902,846 | 2/1990 | DiLeo et al. | 585/525 |
| 4,935,570 | 6/1990 | Nelson et al. | 585/329 |
| 4,950,822 | 8/1990 | DiLeo et al. | 585/310 |
| 4,956,512 | 9/1990 | Nissfolk et al. | 585/521 |
| 4,956,513 | 9/1990 | Walker et al. | 585/525 |
| 4,981,578 | 1/1991 | Lycer et al. | 585/525 |
| 4,982,026 | 1/1991 | Karn et al. | 585/18 |
| 5,068,487 | 11/1991 | Theriot | 585/510 |
| 5,095,172 | 3/1992 | Lanier et al. | 585/525 |
| 5,191,140 | 3/1993 | Akatsu et al. | 585/525 |
| 5,225,588 | 7/1993 | Senaratne et al. | 560/71 |
| 5,241,085 | 8/1993 | Senaratne et al. | 549/396 |
| 5,250,750 | 10/1993 | Shubkin et al. | 174/17 LF |
| 5,288,933 | 2/1994 | Kao et al. | 585/513 |
| 5,396,013 | 3/1995 | Theriot | 585/510 |
| 5,420,373 | 5/1995 | Hope et al. | 585/525 |

*Primary Examiner*—Jacqueline V. Howard
*Attorney, Agent, or Firm*—James R. Henes; Stephen L. Hensley

[57] ABSTRACT

Alpha-olefin oligomers are produced by oligomerizing an alpha-olefin monomer with a catalyst system comprising boron trifluoride, a protic promoter, and a modifier which is (a) at least one 1,3-dioxolane, or (b) at least one 1,3-dioxane, or (c) a combination of (a) and (b). Use of these modifiers in the $BF_3$-catalyzed oligomerization makes it possible to modify the promoted catalytic reaction so that product containing as much as 50% or more of dimer can be produced at high conversions, at modest reaction temperatures, and in short reaction periods.

22 Claims, No Drawings

OLEFIN OLIGOMERIZATION PROCESS

TECHNICAL FIELD

This invention relates generally to the preparation of alpha-olefin oligomers which are useful as synthetic lubricants and functional fluids. More particularly, this invention relates to $BF_3$-promoter catalyst systems which use a modifier to control the oligomer product distribution and provide higher percentages of lower oligomers, especially dimers.

BACKGROUND

Alpha-olefin oligomers and their use as synthetic lubricants are well-known. The oligomers are usually hydrogenated in order to improve their stability. Early reports of such oligomeric synthetic lubricants appear in Seger et al. U.S. Pat. No. 2,500,161 and Garwood U.S. Pat. No. 2,500,163.

Oligomerization of alpha-olefins in a Group IV metal oxide bed using a $BF_3$-protic promoter catalyst is described in U.S. Pat. No. 2,766,312. Promoters referred to therein include water, carboxylic acid, alkyl halides, alcohols and ethers.

U.S. Pat. No. 2,806,072 discloses the dimerization of $C_6$–$C_{12}$ polypropylenes using a preformed $BF_3$-dialkyl ether catalyst.

Oligomerization of olefins using $BF_3$-promoter catalyst complexes of acid anhydrides, esters, ketones and aldehydes is described in U.S. Pat. No. 3,382,291.

U.S. Pat. No. 3,769,363 to Brennan discloses oligomerization of $C_6$–$C_{12}$ normal alpha-olefins, such as 1-decene, with $BF_3$ and $C_5$ carboxylic acid to improve trimer yields.

U.S. Pat. No. 3,997,621 also to Brennan describes oligomerization of $C_6$–$C_{12}$ normal alpha-olefins with $BF_3$ using alcohols or water promoters in conjunction with small amounts of methyl and ethyl esters of a $C_2$–$C_5$ monocarboxylic acid to improve trimer yields.

In U.S. Pat. No. 4,172,855 $BF_3$-promoter catalysts for grafting a second alpha-olefin onto a $C_6$–$C_{12}$ alpha-olefin dimer to form a low volatility lubricating oil is described. The promoters include glycol ethers such as ethylene glycol monomethyl ether and propylene glycol monoethyl ether, and diisobutyl ether.

U.S. Pat. No. 4,218,330 to Shubkin describes dimerization of $C_{12}$–$C_{18}$ alpha-olefin monomer with a $BF_3$-water complex and an excess of $BF_3$. Unreacted monomer is distilled from the reaction product leaving mainly dimer with minor amounts of trimer and higher oligomers. The product is hydrogenated for use as a lubricant.

U.S. Pat. No. 4,436,947 to Morganson et al. discloses oligomerization of $C_6$–$C_{20}$ olefins, such as 1-decene, with $BF_3$ and a mixture of an aliphatic alcohol, an aliphatic ketone, and a polyol. The product is mainly trimer.

U.S. Pat. No. 4,982,026 to Karn describes polymerization of $C_2$–$C_6$ alkene monomers with $BF_3$ and a strong acid, such as phosphoric acid to produce a polymer having a molecular weight of from 250 to 500 and having a high vinylidene content.

U.S. Pat. No. 5,068,487 describes a process for producing products containing predominately dimers and trimers of alpha-olefins using a $BF_3$ catalyst promoted by an alcohol alkoxylate.

U.S. Pat. No. 5,191,140 discloses a process for making alpha-olefin oligomers by use of $BF_3$ promoted by at least two of water, alcohols and anhydrides to peak the reaction at lower molecular weight product.

In U.S. Pat. No. 5,396,013 it is shown that polyethers will moderate promoted $BF_3$-catalyzed oligomerizations to provide either predominately dimer- or trimer-containing oligomers.

U.S. Pat. No. 5,420,373 discloses a process for producing predominately dimer and trimer from $C_6$–$C_{20}$ olefins, such as 1-decene, with $BF_3$ and a hydroxy carbonyl promoter— i.e., a hydroxy ketone or a hydroxy aldehyde. Secondary promoters may also be used, namely aldehydes, alcohols, alcohol alkoxylates, carboxylic acids, ethers, ketones, and their mixtures.

The particular application for which the oligomer oils are used depends largely upon their viscosity, with viscosities of about 2–10 cSt at 100° C. being preferred for general lubricating oil applications. These materials are, in general, mixtures of different percentages of dimer, trimer, tetramer, pentamer and, in the case of the higher viscosity products in this range, higher oligomers as well. To increase viscosity, processes are used which either produce more of the higher oligomers or some of the lower oligomers are removed such as by distillation.

Most lower viscosity dimer products are obtained as by-products of the production of higher viscosity synthetic oils. Because of increasing use of dimers in applications such as low temperature lubricants and drilling fluids, methods for their preferential production are of particular interest. Although higher oligomerization temperatures tend to increase dimer formation, use of such higher temperatures can cause corrosion of process equipment.

SUMMARY OF THE INVENTION

New, highly effective modifiers for $BF_3$-catalyzed oligomerization reactions have been discovered. By the practice of preferred embodiments of this invention it has been found possible to modify the promoted catalytic reaction so that product containing as much as 50% or more of dimer can be produced at high conversions, at modest reaction temperatures, and in short reaction periods.

The modifiers employed pursuant to this invention are 1,3-dioxolanes and 1,3-dioxanes.

Accordingly, in one of its embodiments this invention provides a process of preparing alpha-olefin oligomer which comprises contacting an alpha-olefin monomer which contains from about 6 to about 20 carbon atoms with a catalyst system comprising boron trifluoride, a protic promoter, and a 1,3-dioxolane or a 1,3-dioxane, or a combination thereof.

In a preferred embodiment the foregoing process is conducted under oligomerization conditions forming a reaction mixture that contains 50% or more of dimer, terminating the oligomerization in said reaction mixture, and recovering the dimer from said reaction mixture, for example, by distillation. It has been found possible to conduct the process whereby at an alpha-olefin conversion above 90%, oligomerization reaction product mixtures containing over 60% of dimer and over 90% of combined dimer and trimer are formed, and this constitutes a particularly preferred embodiment of this invention.

Another preferred embodiment utilizes water and/or at least one alkanol as the catalyst promoter in each of the foregoing processes.

Still another preferred embodiment involves conducting a process of this invention using as the protic promoter an alcohol alkoxylate such as described in U.S. Pat. No. 5,068,487.

The above and other embodiments and features of this invention will become still further apparent from the ensuing description and appended claims.

FURTHER DESCRIPTION

The olefins used in making the oligomers are predominately (at least 50 mole %) $C_6$–$C_{20}$ straight chain (i.e., linear) monoolefinically unsaturated hydrocarbons in which the olefinic unsaturation exists in the 1- or alpha-position of the straight chain. Such alpha-olefins are available as articles of commerce, and can be made by thermal cracking of paraffinic hydrocarbons or by well-known Ziegler ethylene chain growth technology. Individual olefins can be used as well as mixtures of such olefins. Examples of olefins that can be used are 1-hexene, 1-heptene, 1-octene, 1-nonene, 1-decene, 1-undecene, 1-dodecene, 1-tridecene, 1-tetradecene, 1-hexadecene, 1-octadecene, 1-eicosene, and mixtures of two or more of such 1-olefins. Remotely branched 1-olefins such as 5-methyl-1-heptene, 6-methyl-1-heptene, 6-methyl-1-octene, 7-methyl-1-octene, 6,7-dimethyl-1-octene, 7,7-dimethyl-1-octene, 8-methyl-1-nonene, and like 1-olefins can also be used especially when used together with linear 1-olefins. The more preferred olefins are linear alpha-olefin monomers containing about 8–14 carbon atoms. The most preferred 1-olefin monomer is 1-decene.

Minor amounts of up to about 50, and usually less than 25 mole % of internal and/or vinylidene olefins can be present in the olefin monomers.

Oligomerization is effected by contacting the monomer(s) with a catalytic amount of boron trifluoride, which typically is at least about 0.002 moles per mole of olefin, together with a protic promoter and a modifier. Preferably the reaction is performed in a reaction mixture saturated with boron trifluoride or in a sealed agitated reactor under an atmosphere enriched in boron trifluoride.

Among the protic promoters that can be used are water, carboxylic acids, mineral acids, alcohols, phenols, carboxylic acid esters and anhydrides, ketones, aldehydes, hydroxy ketones, hydroxy aldehydes, alcohol alkoxylates, and mixtures of any two or more of the foregoing. Preferred are water, $C_1$ to $C_{24}$ alcohols and, more preferably, $C_1$ to $C_{12}$ alcohols, and alcohol alkoxylates such as described in U.S. Pat. No. 5,068,487. Examples of preferred alcohols include methanol, ethanol, 1-propanol, 2-propanol, 1-butanol, 2-methyl-1-propanol, 1-pentanol, 2-pentanol, 1-hexanol, 2-hexanol, 1-heptanol, 1-octanol, 2-ethyl-1-hexanol, 1-nonanol, 1-decanol, 1-undecanol, 1-dodecanol, and mixtures of two or more $C_1$ to $C_{12}$ alcohols. Of these, 1-propanol and 1-butanol are particularly preferred. Examples of alcohol alkoxylates include 2-methoxyethanol, 2-ethoxyethanol, 1-methoxy-2-propanol, 4-ethoxy-1-butanol, 2-butoxyethanol, and their analogs and homologs. The protic promoter is used in an oligomerization-promoting amount, i.e., an amount that causes the $BF_3$ to function as an oligomerization catalyst, such as for example from about 0.001 to about 0.04 moles per mole of alpha-olefin monomer(s). In general the $BF_3$ is used in a molar excess relative to the quantity of promoter(s) used, typically by maintaining a pressurized atmosphere of $BF_3$ or $BF_3$ and nitrogen in the reaction vessel. The promoter can be mixed with the olefin feed or the promoter can be charged separately to the reactor, either entirely at the outset or portionwise as the oligomerization proceeds.

The 1,3-dioxolanes used in the practice of this invention, also known as ethylene or propylene ketals, have a saturated five- or six-membered ring composed of three or four carbon atoms, respectively, and two oxygen atoms in the 1- and 3-positions. The ring carbon atoms can either contain two hydrogen atoms each or one or more such carbon atoms can be substituted by one or two hydrocarbyl groups. Examples of such compounds include 1,3-dioxolane, 2-methyl-1,3-dioxolane, 4-methyl-1,3-dioxolane, 2-ethyl-1,3-dioxolane, 4-ethyl-1,3-dioxolane, 2-butyl-1,3-dioxolane, 2,2-dimethyl-1,3-dioxolane, 2,4-dimethyl-1,3-dioxolane, 2-ethyl-4-methyl-1,3-dioxolane, 4,4-diethyl-1,3-dioxolane, 2-butyl-4-methyl-1,3-dioxolane, 4-butyl-2-methyl-1,3-dioxolane, 4,5-dimethyl-1,3-dioxolane, 2-phenyl-1,3-dioxolane, 2-o-tolyl-1,3-dioxolane, 2-p-tolyl-1,3-dioxolane, 2,4,5-trimethyl-1,3-dioxolane, 2,2,4,5-tetramethyl-1,3-dioxolane, 1,3-dioxane, 2-methyl-1,3-dioxane, 4-methyl-1,3-dioxane, 5-methyl-1,3-dioxane, 2-ethyl-1,3-dioxane, 4-ethyl-1,3-dioxane, 5-ethyl-1,3-dioxane, 2-butyl-1,3-dioxane, 2,2-dimethyl-1,3-dioxane, 2,4-dimethyl-1,3-dioxane, 2,5-dimethyl-1,3-dioxane, 2,6-dimethyl-1,3-dioxane, 4,5-dimethyl-1,3-dioxane, 2-ethyl-4-methyl-1,3-dioxane, 4,4-diethyl-1,3-dioxane, 2-butyl-4-methyl-1,3-dioxane,4-butyl-2-methyl-1,3-dioxane, 4,5-dimethyl-1,3-dioxane, 2-phenyl-1,3-dioxane, 2-o-tolyl-1,3-dioxane, 2-p-tolyl-1,3-dioxane, 2,4,5-trimethyl-1,3-dioxane, 2,4,6-trimethyl-1,3-dioxane, 2,2,4,5-tetramethyl-1,3-dioxane, and their analogs and homologs. A mixture of two or more 1,3-dioxolanes, or a mixture of two or more 1,3-dioxanes can be used. Similarly a mixture of (a) one or more 1,3-dioxolanes and (b) one or more 1,3-dioxanes can be used. Typically the 1,3-dioxolanes and 1,3-dioxanes used in the practice of this invention individually contain a total of up to about 20 carbon atoms per molecule. Preferred are 1,3-dioxolane, 1,3-dioxane, 1,3-dioxolanes having from 1 to 6 methyl substituents on the ring, and 1,3-dioxanes having from 1 to 8 methyl substituents on the ring, such as for example 2-methyl-1,3-dioxolane, 2,2,4-trimethyl-1,3-dioxolane, 4-methyl-1,3-dioxane, 2,4-dimethyl-1,3-dioxane, and 5,5-dimethyl-1,3-dioxane. A particularly preferred modifier is 2,2-dimethyl-1,3-dioxolane.

The modifiers may contain additional functionality in the molecule, provided the functionality is such that it does not significantly impair the effectiveness of the modifier. Side chain linkages or substituents on one or more of the ring carbon atoms of the modifier that do not impair the effectiveness of the modifier and that thus can be present therein are the following: halide, hydrocarbyloxy, hydrocarbylthio, ether oxygen linkage, thioether sulfur linkage, nitro, hydrocarbylsilyl, carbonyl, and thiocarbonyl.

A few examples of modifiers having additional non-harmful functionality are:

2-chloromethyl-1,3-dioxolane 2-fluoromethyl-1,3-dioxolane 2-trichloromethyl-1,3-dioxolane 2-p-chlorophenyl-1,3-dioxolane 2-(2-bromoethyl)-1,3-dioxane 4-(4-chlorophenyl)-4-methyl-1,3-dioxane 5,5-dimethyl-2-nitromethyl-1,2-dioxane 2-{2-(benzyloxy)ethyl}-5,5-dimethyl-1,3-dioxane.

In general, the preferred modifiers are those that contain no additional functionality in the molecule.

While normally a single modifier is used in the process of this invention, suitable mixtures of two or more modifiers can be employed, if desired.

In conducting the process of this invention the alpha-olefin or mixture of alpha-olefins, boron trifluoride, protic promoter and modifier can be charged to the reactor in any suitable sequence. Preferably, however, the modifier should be present before any substantial amount of oligomerization has occurred. In this way the maximum beneficial reaction modifying effect of the modifier can be realized.

The reaction can be carried out as a batch, continuous, or semi-continuous process at temperatures which typically are in the range of 0° to 200° C., and preferably in the range of about 30° to about 150° C. More preferably, the temperature is maintained in the range of about 30° to about 60° C., and especially in the range of about 40° to about 60° C. The reaction is typically conducted at pressures ranging from atmospheric up to, for example, 1000 psig, and preferably in the range of about 5 to about 100 psig. The progress of the reaction can be monitored, if desired, by taking samples of the oligomerization mixtures at suitable periods during the course of the reaction and subjecting the sample to gas chromatographic (GC) analysis. In this connection, all references in this specification and in the claims to percentages of oligomer components in the oligomerization reaction product mixture and to olefin conversion percentages are based on GC area percentages in which the analyses are conducted using a Hewlett Packard 5890 gas chromatograph equipped with a flame ionization detector and a methyl siloxane column operated under the following conditions: initial temperature=100° C.; final temperature=350° C.; Rate=15° C./minute.

The reaction can be conducted in a single stirred reactor or in a series of reactors.

To terminate the oligomerization reaction when the desired product distribution and olefin conversion have been achieved, the dimer enriched reaction mixture can be quenched with or in water or an aqueous solution, such as a solution of a salt or a base, or more preferably a solution of a strong base such as sodium hydroxide or potassium hydroxide. The organic phase is recovered and unless the oligomeric product is to be used in the form produced, the reaction product is distilled to recover the product fraction(s) desired. Unreacted olefin can be recovered and recycled.

In most cases the modifiers are used in proportions relative to the promoter that will peak the oligomerization at the dimer stage, but in some cases the proportions can be adjusted for peaking at the trimer stage. Thus in general the ratio of modifier to promoter will usually fall somewhere within the range of from about 0.1 to about 10 moles of modifier per mole of promoter, and typically within the range of from about 0.5 to about 2 moles of modifier per mole of promoter. For producing product highly enriched in dimer, the preferred proportions fall in the range of from about 0.75 to about 1.25 moles of modifier per mole of promoter. It should be understood that one should use a suitable ratio for achieving the particular results desired under the particular reaction conditions and with the particular materials selected for use. Thus the ratio that will best serve the needs of the situation at hand can be determined by performing a few oligomerizations using procedures such as given in the following illustrative examples.

EXAMPLES

1-Decene, 1-butanol (1.0 mole % based on 1-decene) and the amount of 2,2-dimethyl-1,3-dioxolane modifier ("DMD") given in Table I, are charged to a reactor equipped with cooling means, stirring means and inlet/outlet ports. The reactor is sealed and pressurized (10 psig) with boron trifluoride, and the temperature of the stirred mixture is maintained at 50° C. by external cooling for the duration of the reaction. Periodic samples are taken for GC analysis to monitor the progress of the reaction. To terminate the reaction, the reactor is vented into a caustic scrubber, purged with nitrogen, and the reactor contents are drained into 10% aqueous caustic solution. The product is then washed twice with water. The final product mixture is analyzed by GC for product composition.

For comparative purposes the results using dibutyl ether ("DBE") in lieu of a 1,3-dioxolane are also given the Table I. The Control of Table I was a run carried out in the same manner as the above examples except that no modifier was used.

TABLE I

| Example | Modifier (mole %) | Time, min. | $C_{20}$, % | $C_{30}$, % | $C_{40}$, % | $C_{50}$, % | Conversion, % |
|---|---|---|---|---|---|---|---|
| 1 | DMD (1.0) | 90 | 62.0 | 28.7 | 5.6 | 0.5 | 96.8 |
| 2 | DMD (1.0) | 120 | 56.2 | 29.7 | 10.7 | 0.7 | 97.3 |
| 3 | DMD (0.5) | 60 | 55.2 | 34.4 | 6.6 | 0.6 | 96.7 |
| 4 | DMD (0.5) | 120 | 42.2 | 37.2 | 16.8 | 1.2 | 97.4 |
| Comp. | DBE (1.0) | 120 | 21.8 | 54.9 | 14.4 | 4.9 | 96.2 |
| Control | None | 120 | 11.8 | 65.2 | 16.7 | 3.8 | 97.6 |

It will be noted from a comparison among the results of Examples 1–4 that the shorter reaction periods favored higher yields of the dimer, while at the same time giving high olefin conversions. When compared with the results from the comparative run using DBE, the results of Examples 1–4 illustrate the substantially enhanced effectiveness of 1,3-dioxolanes in providing high yields of dimer at high olefin conversions and in short reaction periods.

The entire disclosure of each and every U.S. patent referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of preparing alpha-olefin oligomer enriched in dimer which comprises contacting an oligomerizable predominantly linear alpha-olefin monomer with a catalyst system comprising boron trifluoride, a protic promoter, and a modifier which is (a) at least one 1,3-dioxolane, or (b) at least one 1,3-dioxane, or (c) a combination of (a) and (b), in an amount within the range of from about 0.1 to about 10 moles of modifier per mole of promoter, at a temperature in the range of 0° to 200° C. and a pressure in the range of atmospheric to 100° psig, to form an oligomerization product mixture containing at least about 50% of the dimer of the aforesaid linear alpha-olefin, and terminating the oligomerization.

2. A process according to claim 1 wherein the protic promoter is water and/or at least one alcohol.

3. A process according to claim 1 wherein the oligomerization forms a final reaction product mixture that contains 50% or more of dimer at an olefin conversion of at least 90%.

4. A process according to claim 1 wherein the protic promoter is an alcohol alkoxylate.

5. A process according to claim 1 wherein the alpha-olefin is predominately linear alpha-olefin having from 8 to 14 carbon atoms.

6. A process according to claim 1 wherein the alpha-olefin is 1-decene.

7. A process according to claim 1 wherein the modifier is 1,3-dioxolane or 1,3-dioxolane having from 1 to 6 methyl substituents on the ring.

8. A process according to claim 1 wherein the modifier is 1,3-dioxane or 1,3-dioxane having from 1 to 8 methyl substituents on the ring.

9. A process according to claim 1 wherein the modifier is 2,2-dimethyl-1,3-dioxolane.

10. A process of preparing alpha-olefin oligomer enriched in dimer which comprises contacting an oligomerizable predominantly linear alpha-olefin monomer with a catalyst system comprising boron trifluoride, a protic promoter, and (a) at least one 1,3-dioxolane modifier, or (b) at least one 1,3-dioxane modifier, or (c) a combination of (a) and (b), in an amount within the range of from about 0.1 to about 10 moles of modifier per mole of promoter, at a temperature in the range of about 0° to about 200° C., and under an atmosphere comprising boron trifluoride at a pressure in the range of about atmospheric to about 1000 psig, to form an oligomerization product mixture containing at least about 50% of the dimer of the aforesaid linear alpha-olefin, and terminating the oligomerization.

11. A process according to claim 10 wherein the alpha-olefin monomer is predominately linear alpha-olefin.

12. A process according to claim 10 wherein the protic promoter is an alcohol or alcohol alkoxylate or a combination thereof.

13. A process according to claim 10 wherein the alpha-olefin is 1-decene.

14. A process according to claim 10 wherein the alpha-olefin monomer is predominately linear alpha-olefin, wherein the protic promoter is an alcohol, wherein the temperature is maintained in the range of about 20° to about 60° C. throughout substantially the entire reaction, and wherein the pressure is maintained in the range of about 5 to about 100 psig throughout substantially the entire reaction.

15. A process of preparing alpha-olefin oligomer enriched in dimer which comprises oligomerizing a predominately linear alpha-olefin monomer having in the range of 8 to 14 carbon atoms in the molecule with a catalyst system comprising boron trifluoride, a protic promoter, and (a) at least one 1,3-dioxolane modifier, or (b) at least one 1,3-dioxane modifier, or (c) a combination of (a) and (b) at a temperature in the range of about 30° to about 150° C., under an atmosphere comprising boron trifluoride at a pressure in the range of 5 psig to about 100 psig, and in proportions in the range of about 0.5 to about 2 moles of modifier per mole of promoter, that form an oligomerization product mixture containing at least about 50% of dimer of the aforesaid linear alpha-olefin monomer, and terminating the oligomerization in said reaction mixture.

16. A process according to claim 15 wherein the protic promoter is water, an alcohol, an alcohol alkoxylate, or any combination of two or more of these.

17. A process according to claim 15 wherein the alpha-olefin monomer is 1-decene and the protic promoter is an alcohol.

18. A process according to claim 17 wherein the oligomerization is terminated by quenching the said oligomerization product mixture with water or an aqueous solution.

19. A process according to claim 18 wherein said proportions are in the range of about 0.75 to about 1.25 moles of modifier per mole of promoter.

20. A process according to claim 18 wherein said promoter and said modifier are employed in substantially equimolar proportions.

21. A process according to claim 17 wherein the temperature is maintained in the range of about 20° to about 60° C. throughout substantially the entire oligomerization.

22. A process according to claim 21 wherein said proportions are in the range of about 0.75 to about 1.25 moles of modifier per mole of promoter.

* * * * *